US006365621B1

(12) United States Patent
Tanaka et al.

(10) Patent No.: US 6,365,621 B1
(45) Date of Patent: Apr. 2, 2002

(54) REMEDIES OR PREVENTIVES FOR INTRACTABLE EPILEPSY

(75) Inventors: Tatsuya Tanaka, Asahikawa; Akira Takazawa, Mito; Mitsunobu Yoshii; Yoshiya Murashima, both of Tokyo, all of (JP)

(73) Assignee: Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/744,954

(22) PCT Filed: Aug. 6, 1999

(86) PCT No.: PCT/JP99/04264

§ 371 Date: Feb. 6, 2001

§ 102(e) Date: Feb. 6, 2001

(87) PCT Pub. No.: WO00/07593

PCT Pub. Date: Feb. 17, 2000

(30) Foreign Application Priority Data

Aug. 6, 1998 (JP) .......................................... 10-223233

(51) Int. Cl.$^7$ ..................... A61K 31/40; C07D 401/12; C07D 207/12
(52) U.S. Cl. .................... 514/423; 514/343; 546/278.4; 548/568
(58) Field of Search ...................... 546/278.4; 548/568; 514/343, 408, 423

(56) References Cited

U.S. PATENT DOCUMENTS 4,341,790 A * 7/1982 Betzing et al. ............. 546/281

OTHER PUBLICATIONS

19th Japanese Neuroscience Congress, Yoshiya L. Murashima et al., Dept of Neurophysiol, Tokyo Inst. of Psychiat. Tokyo 156, Japan, New Product Res. Lab. III. Daiichi Pharmaceutical Co. Ltd. Tokyo 134, Japan.

Antiepileptic Effects of Nootropic Agent, Nefiracetam–In Vivo Study of Epileptic Mutant, el Mice, Yoshiya L. Murashima et al., Dept of Neurophysiol, Tokyo Inst. of Psychiat. Tokyo 156, Japan, New Product Res. Lab. III. Daiichi Pharmaceutical Co. Ltd. Tokyo 134, Japan.

Effects of the nootropic nefiracetam on rat hippocampal GABA release, Yoshiya L. Murashima et al., Dept of Neurophysiol, Tokyo Inst. of Psychiatry, 2–1–8 Kamikitazawa, Setagaya–ku, Tokyo 156, Japan, Tokyo R & D Center, Daiichi Pharmaceutical Co., Ltd. 1–16–13 Kitakasai, Edogawa–ku, Tokyo 134, Japan.

* cited by examiner

Primary Examiner—Zinna Northington Davis
(74) Attorney, Agent, or Firm—Oblon, Spivak, McClelland, Maier & Neustadt, P.C.

(57) ABSTRACT

A therapeutic or preventive agent for intractable epilepsy comprising as an active ingredient a compound represented by $R^2$—$CH_2CONH$—$R^1$ (I), wherein $R^1$ is a phenyl group or a pyridyl group, which may have a substituent and $R^2$ is a 2-oxo-1-pyrrolidinyl group which may have a substituent.

11 Claims, No Drawings

REMEDIES OR PREVENTIVES FOR INTRACTABLE EPILEPSY

This application is a 371 of PCT/JP99/04264 filed Aug. 6, 1999.

TECHNICAL FIELD

The present invention relates to a therapeutic or preventive agent for, among other epilepsies, intractable epilepsies, which are difficult to prevent or treat by existing antiepileptics.

BACKGROUND ART

Epilepsy is a chronic brain disease in which epileptic seizures are the predominant feature. Generally, most epilepsies and diseases associated therewith are difficult to treat, since epilepsies are not etiologically elucidated. Thus, administration of an antiepileptic agent is a common approach toward suppressing epileptic seizures or inhibiting propagation of focal seizures to other portions.

At present, more than ten types of antiepileptic agents are available in Japan. Yet, many different intractable epilepsies cannot be successfully suppressed by antiepileptic agents, including so-called "resistant-to-therapy" seizures and cases in which drug compliance cannot be obtained due to side effects despite satisfactory suppression of seizures. Thus, there is still demand for an antiepileptic agent which is more effective than existing ones and which exhibits fewer and less severe side effects (see "Mechanismus of Action Antiepileptics," *Clinical Psychiatry Courses*, Nakayama-Shoten, authored by Akira TAKAZAWA, et al.).

Therefore, an object of the present invention is to provide a pharmaceutical effective for intractable epilepsies or a seizure associated therewith, for which existing antiepileptics have not exhibited satisfactory efficacy.

DISCLOSURE OF THE INVENTION

The present inventors have conducted extensive studies, and have found that a pyrrolidinylalkylcarboxylic acid amide derivative represented by formula (I) serves as a pharmaceutical which is efficacious in the treatment or prevention of intractable epilepsies. The present invention has been accomplished based on this finding.

Accordingly, the present invention provides a therapeutic or preventive agent for an intractable epilepsy or a seizure associated therewith comprising as an active ingredient a compound represented by the following formula (I):

$$R^2\text{—}CH_2CONH\text{—}R^1 \quad (I)$$

wherein $R^1$ is a phenyl group or a pyridyl group, either of which may have one or more substituents which may be identical to or different from one another and which are selected from among a C1–C3 alkyl group and a hydroxyl group, and $R^2$ is a 2-oxo-1-pyrrolidinyl group which may have one or more substituents, wherein said one or more substituents may be identical to or different from one another and are selected from among a halogen atom, a hydroxyl group, and a C1–C3 alkyl group; a salt thereof; or a hydrate of the compound or the salt.

The present invention also provides an inhibitor which limits a motor seizure associated with an epilepsy (in terms of duration of an epileptic symptom); an inhibitor for propagation of an epileptic seizure; and a therapeutic or preventive agent for epilepsy having a function of raising a seizure-inductive threshold, each of the above three types of agents comprising as an active ingredient a compound represented by the formula (I), a salt thereof, or a hydrate of the compound or salt. The present invention provides use of a compound represented by the following formula (I); a salt thereof; or a hydrate of the compound or salt, for producing a therapeutic or preventive agent for an intractable epilepsy or a seizure associated therewith.

The present invention also provides use of a compound represented by the following formula (I); a salt thereof; or a hydrate of the compound or salt, for producing a suppresser which limits a motor seizure associated with an epilepsy (in terms of duration of a epileptic symptom); a suppresser for propagation of an epileptic seizure; and a therapeutic or preventive agent for epilepsy having a function of raising a seizure-inductive threshold.

The present invention provides a method for treating an intractable epilepsy or a seizure associated therewith through administration of a compound represented by the following formula (I); a salt thereof; or a hydrate of the compound or salt.

The present invention, also provides a method for treatment for inhibiting a motor seizure associated with an epilepsy (in terms of duration of a epileptic symptom); a method for treatment for preventing propagation of an epileptic seizure; and a method for treating epilepsy involving a function of raising a seizure-inductive threshold, by the administration of a compound represented by the following formula (I); a salt thereof; or a hydrate of the compound or salt.

BEST MODE FOR CARRYING OUT THE INVENTION

The substituents in formula (I) will next be described. $R^1$ represents a pyridyl group, a substituted pyridyl group, a phenyl group, or a substituted phenyl group. Of these, a phenyl group or a substituted phenyl group is preferred as $R^1$. The one or more substituents for a phenyl group may be identical to or different from one another and are selected from among a C1–C3 alkyl group, a halogen atom, and a hydroxyl group. Of these, a methyl group and a hydroxyl group are preferred. Furthermore, two methyl groups or a combination of two methyl group and one hydroxyl group are preferred, and the preferable positions of substitution are 2- and 6-positions of a phenyl group. Thus, a 2,6-dimethylphenyl group is particularly preferred. The one or more substituents for a pyridyl group may be identical to or different from one another and are selected from among a halogen atom, a C1–C3 alkyl group, an acyl group, etc.

$R^2$ is a 2-oxo-1-pyrrolidinyl group which may have one or more substituents. The one or more substituents may be identical to or different from one another and are selected from among a halogen atom, a C1–C3 alkyl group, and a hydroxyl group. Of these, a hydroxy-substituted-2-oxopyrrolidinyl group and 2-oxopyrrolidinyl group are particularly preferred.

A typical example of the compound represented by formula (I) is N-(2,6-dimethylphenyl)-2-(2-oxo-1-pyrrolidinyl) acetamide (generic name: nefiracetam), a salt thereof, and a hydrate of the compound or salt.

A process for producing nefiracetam has already been disclosed in Japanese Patent Application Laid-Open (kokai) Nos. 56-2960, 61-280470, and 6-65197.

Nefiracetam finds pharmaceutical use as, for example, a cerebovascular dementia-ameliorating agent (Japanese Patent Application Laid-Open (kokai) No. 56-163145), an ameliorating agent for dementia of Alzheimer type (Japanese Patent Application Laid-Open (kokai) No. 5-163144), or a stabilizing agent for the mitochondrial membrane (Japanese Patent Application No. 8-260649). The working mechanism of nefiracetam is partially disclosed in Japanese Patent Application No. 9-249131.

An antiepileptic action provided by nefiracetam has already investigated through a test employing EL mice as models, and potential use as an antiepileptic agent is indicated (the 17th Convention of Japanese Neuroscience Society, 3i, 1993; the 23rd Society for Neuroscience, 1993, 11; and the 26th Society for Neuroscience, Nov. 16, 1996, Washington D.C.).

The model of epilepsy employing EL mice tested in the above reports is a model of epilepsy caused by a congenital genetic disposition formed through mutation. The model exhibits perception-evoked secondary generalization of a seizure and stupor after tonic or clonic convulsion. An electroencephalogram of the model shows characteristic changes corresponding to the above states. In addition, the model of epilepsy is a genetic model, to thereby serve as a useful model for investigating epileptic states induced by genetic disposition.

However, no clinically defined types of epilepsies of humans correspond to the EL mouse model, although efficacy of a pharmaceutical to suppress epilepsy is easily attained for EL mice through administration of a pharmaceutical in a small dose. Therefore, the pharmaceutical is not always clinically effective for humans even though the efficacy is proven for EL mice. Particularly, since a clinical effect of a pharmaceutical on intractable epilepsy of humans still involves an unknown issue, the model is not suitable for evaluating the prospects of the clinical effect.

In view of the foregoing, the present inventors have conducted earnest studies, and have found that the compound represented by formula (I) suppresses not only a focal seizure but also a secondary generalized seizure in a model of focal epilepsy, which has been difficult to treat by use of a conventional therapeutic agent. Accordingly, an object of the present invention is to provide a suppresser for focal epilepsies; a suppressor for secondary generalization; and a therapeutic or preventive agent for intractable epilepsies.

Thus, the present invention relates to a therapeutic or preventive agent for intractable epilepsies. First, an explanation of "intractable epilepsy" will be given below.

The characteristics of intractable epilepsy include 1) high occurrence of partial seizure followed by a generalized seizure (particularly temporal lobe epilepsy); 2) high occurrence of symptomatic epilepsy caused by an organic lesion in the brain; 3) long-term absence of treatment from the onset to consultation of a specialist and high occurrence of seizures; and 4) high occurrence of status epilepticus in the anamnesis. In other words, the temporal lobe is likely to be a portion of the brain responsible for intractable epilepsy. It is indicated that epilepsy becomes more intractable by changing of the nature thereof and evolving as acquired seizures are repeated.

Intractable epilepsy is categorized into three clinical types, i.e., (a) localization-related epilepsies and syndromes, (b) generalized epilepsies and syndromes, and (c) epilepsies and syndromes undetermined, whether focal or generalized.

Examples of (a) localization-related epilepsies and syndromes include temporal lobe epilepsies, frontal lobe epilepsies, and multi-lobe epilepsies. Temporal lobe epilepsies and frontal lobe epilepsies are typical examples of intractable epilepsy. Multi-lobe epilepsies are considered to be caused by two or more lobes.

Examples of (b) generalized epilepsies and syndromes include Lennox-Gastaut syndrome, West syndrome, and myoclonic epilepsy.

Examples of (c) epilepsies and syndromes undetermined, whether focal or generalized, include severe myoclonic epilepsy in infancy, which exhibits a variety of seizure types. In particular, tonic-clonic seizures frequently occur, to thereby often lead to status epilepticus. Thus, special treatment conducted by a specialist for epilepsy is strongly required (Masako WATANABE, et al., Igakuno Ayumi, 183(1):103–108, 1997).

Seizures associated with intractable epilepsy are categorized into a variety of types, e.g., tonic seizures, tonic-clonic seizures, atypical absence seizures, atonic seizures, myoclonic seizures, clonic seizures, simple partial seizures, complex partial seizures, and secondary generalized seizures. Of these, for tonic and atonic seizures, attention must be paid to injuries resulting from falls.

In addition, complex partial seizures may cause a behavior-caused accident during disturbance of consciousness. In intractable epilepsies, "complex partial seizures" associated with temporal lobe epilepsies and frontal lobe epilepsies occur at relatively high frequency in adults. Although said seizures occur at low frequency in children, the seizures are also intractable as in the case of adults (Progress of Epileptology, No. 2, Haruo AKIMOTO and Toshio YAMAUCHI, Iwanami Gakujutsu Shuppan, 1991, p 51–85).

In the present description, the term "intractable epilepsy" refers to epilepsies or seizures associated therewith corresponding to the following four epilepsies or seizures associated therewith:

(1) epilepsies difficult to treat in which suppression of seizures associated therewith cannot be controlled through a conventional pharmaceutical treatment (Masako WATANABE, et al., Igaku-no Ayumi, 183(1):103–108, 1997);

(2) epilepsies corresponding to the following (a) to (c): (a) localization-related epilepsies such as temporal lobe epilepsis and cortical epilepsis; (b) generalized epilepsies and syndromes such as Lennox-Gastaut syndrome, West syndrome, and myoclonic epilepsy; and (c) epilepsies and syndromes undetermined, whether focal or generalized, such as severe myoclonic epilepsy in infancy;

(3) seizures associated with the above-described intractable epilepsis including tonic seizures, tonic-clonic seizures, atypical absence seizures, atonic seizures, myoclonic seizures, clonic seizures, simple partial seizures, complex partial seizures, and secondary generalized seizures; and (4) epilepsies such as epilepsies following brain surgery, traumatic epilepsies, and relapsed epilepsies following surgery for epilepsy.

The antiepileptic agent of the present invention is effective for the above four types of intractable epilepsies. Of these, the antiepileptic agent of the present invention is particularly effective for localization-related epilepsies corresponding to (2) (a); seizures such as secondary generalized seizures, complex partial seizures and status epilepticus corresponding to (3) and status epilepticus; and epilepsies following brain surgery, traumatic epilepsies, and relapsed epilepsies following surgery for epilepsy corresponding to (4). The antiepileptic agent of the present invention has a possibly excellent effect to epilepsies such as localization-related epilepsies, temporal lobe epilepsies, and cortical epilepsies.

"Temporal lobe epilepsy," which is one type of intractable epilepsy, will next be described.

Temporal lobe epilepsy is an epilepsy having a seizure focus in the temporal lobe, and is categorized under symptomatic and localization-related epilepsies, which also include frontal lobe epilepsies, parietal lobe epilepsies, and occipital lobe epilepsies, based on the international classification of epilepsy.

The syndromes of temporal lobe epilepsy vary in accordance with a focus-localized site and type of seizure propagation, in that the temporal lobe has an anatomically complex structure including neocortex, allocortex, and paleocortex. Temporal lobe epilepsy, as previously defined as a psychomotor seizure, mostly causes complex partial seizures as clinically observed seizures, and also causes simple partial seizures, secondary generalized seizures, and combinations thereof.

Simple partial seizures include autonomic and mental symptoms and sensory symptoms such as olfaction, audition, or vision, sometimes concomitant with symptoms of experiences such as deja-vu and jamais-vu. Complex partial seizures often exhibit motion stopping followed by eating-function automatism, and are divided into amygdala-hippocampus seizures and lateral temporal lobe seizures according to localization. In the case of temporal lobe epilepsy, 70–80% of the seizures are hippocampus seizures, in which aura, motion stopping, lip automatism, and clouding of consciousness are successively developed to result in amnesia. When the focus is in the amygdala, there are caused autonomic symptoms such as dysphoria in the epigastrium; phobia; and olfactory hallucination. Lateral temporal lobe seizures include auditory illusion, hallucination, and a dreamy state, and disturbance of speech when the focus is in the dominant hemisphere. Temporal lobe epilepsy exhibits a long-term psychosis-like state in addition to other symptoms and recognition-and-memory disorder more frequently than do other epilepsies (Medical Dictionary, Nanzando). Treatment of temporal lobe epilepsy is carried out through pharmacotherapy employing a maximum dose of a combination of drugs, or through surgical treatment.

"Cortex epilepsy," which is one type of intractable epilepsy, will next be described. Cortex epilepsy is an epilepsy having a focus in the cerebral cortex, and is classified as symptomatic epilepsy belonging to localization-related (focal) epilepsies and syndromes in the international classification of epilepsy. In the international classification, seizures associated with cortex epilepsy are classified as simple partial seizures, which are partial seizures without reduction of consciousness. Accordingly, an electroencephalogram taken during a seizure associated with cortex epilepsy (not always recorded on the scalp) exhibits localized contralateral electric discharge from the corresponding cortical field. The rate of seizures associated with cortex epilepsy to the entirety of seizures associated with epilepsies is approximately 15%, and about ⅔ thereof are focal motor seizures including Jacksonian seizures (Wada et al.). Cortex epilepsies are mainly caused by cerebral tumor, an aftereffect of cephalotrauma, etc.; or damage during a perinatal period (Medical dictionary, Nanzando). Based on the focus, cortex epilepsy is classified as temporal lobe epilepsy, parietal lobe epilepsy, or occipital lobe epilepsy.

"Traumatic epilepsy," which is one type of intractable epilepsy, will next be described.

Traumatic epilepsy, in a broad sense, is divided into two epilepsies, i.e., "early epilepsy" and "late epilepsy." "Early epilepsy" is caused through stimulation of the brain induced by convulsion within a week after suffering a trauma, and is not a true epilepsy. In contrast, "late epilepsy" is a true epilepsy that is caused one or more weeks after suffering a trauma. Japan produces 100,000–200,000 candidates for traumatic epilepsy per year (Shinya MANAKA, Kyukyu Iryo, 17:1076–1077).

Most of the traumatic epilepsies are caused by formation of a focus at a traumatically damaged portion of the cortex, and they are considered to be typical examples of partial epilepsies. Therefore, treatment thereof is principally based on a pharmacotherapy which is generally employed for treatment of epilepsy. However, since onset and a process of individual symptoms are diverse, in many cases the epilepsy becomes intractable through administration of an antiepileptic agent, as reported in Nihon Saigai Igakukai Kaishi, 32(6):453–460, 1984. Meanwhile, surgical treatment has been employed for actually existing intractable symptoms in which control of a seizure is difficult (Yoshifumi MATSUMOTO, Neurotraumatology, 17:101–106, 1994).

"A secondary generalized seizure," which is one of the symptoms associated with intractable epilepsy, will next be described.

The secondary generalized seizure is one type of partial seizure, which exhibit a clinical syndrome and an electrocephalogram feature observed as excitation of neurons that shows initiation of a seizure in a limited portion of one cerebral hemisphere.

The secondary generalized seizure is initiated as a simple partial seizure (without impairment of consciousness) or a complex partial seizure (with impairment of consciousness), and develops to general convulsion induced through secondary generalization. The main symptom thereof is convulsion such as a tonic-clonic seizure, a tonic seizure, or a clonic seizure (Kazuyoshi WATANABE, the 22th Nou-no Igaku Seibutsugaku Kenkyuukai, 1997. 1. 18).

"A complex partial seizure," which is one of the symptoms associated with intractable epilepsy, will next be described.

The complex partial seizure refers to a partial seizure with impairment of consciousness, and is similar to a seizure that has conventionally been called a psycho-motor seizure or a seizure associated with temporal lobe epilepsy. In the international classification draft (1981), the complex partial seizure is defined as a seizure "with impairment of consciousness exhibiting an electrocephalogram during a seizure in which unilateral or bilateral electric discharge attributed to a focus in a diffuse or a temporal or front-temporal portion."

Actually, the neuromechanism responsible for the above type of seizures is considered to include the amygdala, the hippocampus, the hypothalamus, the parolfactory cortex, etc., in addition to the frontal and temporal lobes. The seizures typically last 1–2 minutes or slightly longer, and the onset and cessation of the seizures are not abrupt but gradual. Examples of complex partial seizures include (1) seizures with reduction of consciousness (gradually evolving impairment of consciousness, arrest of motion, speech, and reaction, and amnesia); (2) cognitive seizures (deja-vu, jamais-vu, ideo-seizures); (3) affective seizures (fear, anger, emptiness, strangeness, delight, joy); (4) psycho-sensory seizures (hallucinations; visual, auditory, gustatory, olfactory, cenesthesia); and (5) psycho-motor seizures (automatism, lip-licking, chewing, stereotypy). The onset of the seizures can be observed, mainly at the age of 10–25, but at any age (Epilepsy, Nihon Bunkakagaku-sha, 49–51, 1996, edited by Haruo AKIMOTO).

"Status epilepticus," which is one type of intractable epilepsy, will next be described.

In status epilepticus, consciousness is not restorable during a seizure associated with epilepsy that lasts for 30 minutes or longer or repeats. Any type of seizure may evolve to status epilepicus. The most common case is a tonic-clonic seizure, and status epilepticus thereof is fatal and must be treated immediately. In many cases, cessation of an antiepileptic agent induces status epilepticus. Thus, an atilepitic agent is administered intravenously while the central nervous system disorder and whole-body conditions are monitored and controlled, and elucidation of the cause and treatment thereof is progressing (Nanzando, Medical Dictionary). Since a status epilepticus convulsion is known to cause intractable epilepsy, immediate and appropriate action is required for the diagnosis of and first aid for a status epilepticus convulsion. Suppression of a convulsive seizure at the early stage is an important key to aftercare (Teruyuki OGAWA, Clinical Pediatrics; 47(12):2673–2681. 1994).

Clinical models for intractable epilepsy of humans are produced by use of animals. Example of such animal models include a "kindling model" and a "Seizures induced by kainic acid."

The "kindling model" serving as a model for intractable epilepsy will be described. When weak electrical stimulation is applied to a certain portion in the brain repeatedly at intervals, evolution of a partial seizure to a generalized seizure is observed. This phenomenon is called kindling. Epileptic origin is formed in the brain while kindling lasts for a long time after cessation of stimulation and sometimes causes a spontaneous epileptic seizure. Although kindling is a long-term phenomenon, no large-scale morphological change of the brain is found. Thus, the kindling model serves as a typical experimental model for epilepsy in that nonspecific epileptic origin involving no tissue damage is acquired in the brain and persists for a long time. By use of such a model, a potentiation process of acquired epileptic origin relating to intractable epilepsy can be investigated, and research can be performed for pathologically specific stages such as onset, continuation, and cessation of seizures; a post-seizure stage; and a seizure-absence stage (Mitsumoto SATO, the 22th Igaku Seibutsugaku Kenkyuukai, resume of lectures, 1997. 1. 18).

A variety of models for epilepsy can be produced from a kindling model, in that a stimulation portion is selectable. The most sensitive portion is the amygdala, which is repeatedly stimulated at a afterdischarge threshold (minimum stimulation intensity) (in general, once per day), to exhibit seizure stages as follows: Stage 1 (chewing); Stage 2 (head nodding); Stage 3 (forelimb clonus); Stage 4 (rearing); and Stage 5 (rearing and falling). Stages 1 and 2 correspond to a complex partial seizure of human temporal lobe epilepsy, and Stages 3 to 5 are considered to be stages of secondary generalized seizure. Stage 5 is regarded as a stage of establishment of kindling. Once kindling is established, susceptibility to electrical stimulation is maintained almost for life.

Kindling is similar to human epilepsy not only in terms of seizure symptoms but also in evaluation of an effect of an antiepileptic agent and the like. Thus, kindling is useful means for understanding of epileptic phenomena. By use of a kindling model having a focus in the limbic system or the cortex, a variety of phenomena can be assured; e.g., an effect on a partial seizure; an effect on an development stage from a partial seizure to a secondary generalized seizure; action mechanisms thereof (such as action for acquisition of epileptogenesis, and neuromechanism relating to generalization of a seizure in the limbic system); and an effect on clinical symptoms. A pharmaceutical effect during a kindling development process toward establishment of a generalized seizure is called "preventive effect," which is evaluated by a preventive effect of a pharmaceutical on acquisition of epileptogenesis. A pharmaceutical effect during a kindling development process involving repeated stimulation after establishment of a generalized seizure is called "therapeutic effect" (Juhn. A. Wada; Mitsumoto SATO, and Kiyoshi MORIMOTO, Neuroscientific Mechanism of Epilepsy Studied with a Kindling Model, p 225–241, 1993). Thus, a kindling model is known as an excellent animal model for the treatment-resistant tempolal lobe epilepsy with a complex partial seizure, a secondary generalized seizure of human.

The present inventors have studied the effects of nefiracetam on an development process of the amygdaloid kindled seizures and on establishment of kindling through a method described below, and have determined the efficacy of nefiracetam. The evolution process of kindling is tested by use of rats, in which electrodes are placed in the amygdala and kindling stimulation (50 Hz sine wave, duration of 1 second, once per day) is applied at specific intervals for restoration. On the first day, an afterdischarge-provocation threshold is determined without administration of a pharmaceutical. From the second day, kindling stimulation having intensity of the afterdischarge-provocative threshold is applied to rats administered with a specimen at a variety of administration doses, to thereby investigate an effect of the specimen on the evolution process of kindling.

Use of nefiracetam as a specimen under such conditions enabled investigation of the effect of nefiracetam on parameters such as a seizure stage and afterdischarge duration on a stimulated side of the amygdala during seizure propagation of amygdala kindling.

The results of such investigation revealed that a group of rats to which nefiracetam had been administered in an amount of 180 mg/kg include a number of rats which do not reach Stage 5 even though the afterdischarge duration is extended, and that a group of rats to which nefiracetam had been administered in an amount of 90 mg/kg exhibit inhibition of stable induction of Stage 5. Although typically the "afterdischarge threshold" is expected to decrease with evolution of kindling, remarkably, approximately half of rats to which nefiracetam had been administered in an amount of 90 mg/kg exhibited a sudden increase in afterdischarge threshold in a process from Stage 3 to Stage 5.

Next, the effects of nefiracetam on a establishment of the amygdala kindled seizures were investigated with regard to the seizure stage, afterdischarge duration, and motor seizure duration, as follows. In order to further clarify the response to the pharmaceutical, the kindling stimulation intensity was used as 1–3 times that of generalized seizure threshold (GST) where Stage 5 is constantly developed.

The results of such investigation revealed that administration of nefiracetam (120 mg/kg) exhibits a strong and significant suppression effect on all parameters under the stimulation intensity equivalent to GST. In the case of a group of rats stimulated at an intensity equivalent to 2-times-GST, a parameter relating to the afterdischarge duration was restored to a value of the non-administration level, and the seizure stage and the motor seizure duration were significantly suppressed. In the case of a group of rats stimulated at an intensity equivalent to 3-times-GST, the afterdischarge duration was restored, and a tendency toward restoration of the seizure stage and the motor seizure duration was proven.

As described above, the effects of nefiracetam depend on the stimulation intensity. Therefore, the effect on suppression of a kindling seizure is indicated to involve two factors;

i.e., increase of the afterdischarge threshold at a seizure-inducing portion and suppression of seizure spreading to the entirety of the brain.

An antiepileptic action of the compound represented by formula (I) was investigated by use of another model, the "Seizures induced by kainic acid (kainate model)," serving as a model for intractable epilepsy. The kainate model is an epileptic model in which kainic acid, which is one of the excitatory amino acids found in the brain, is injected to nuclei (amygdala, hippocampus, etc.) in the limbic system in an microamount to thereby induce focal epilepsy. The kainate model serves as a model for an epileptic seizure; more particularly, as a model for status epilepticus induced from the limbic system in an acute phase, and as a model for evolution of a spontaneous limbic seizure to a secondary generalized seizure in a chronic phase. Thus, the kainate model is recognized as a model for intractable epilepsy. In addition, the model is also employed as a model for intractable human temporal lobe epilepsy in that the model satisfies the following conditions: (a) existence of a focus of epilepsy in tissue (amygdala, hippocampus, etc.) in the limbic system; (b) change in tissue equivalent to hardening of the hippocampus; (c) repeated and continual development of spontaneous complex partial seizure (limbic system seizure); and (d) no therapeutic effect provided by a customary pharmaceutical (edited by Tatsuya TANAKA, *Frontier of Epileptic Research*, p 14, 1994, 1st Japan Winter Conference on Brain Research, Life-Science Publishing). The kainate model may also be used as a cortex epilepsy model through injection of kainic acid to the cortex (sensorymotor field). Furthermore, since local blood flow increases during a epileptic seizure, the correlation between glucose metabolism during status epilepticus of the limbic system and local brain blood flow can be investigated through autoradiography by use of the model, and an effect of the epileptic seizure on a damage of cells can also be investigated.

Although the mechanism of the seizure development in the kainate model is not completely elucidated, the following mechanism is proposed. That is, a proposed mechanism comprises (a) continuation of epileptic stimulation induced by anomalous accumulation of glutamate due to bonding of kainate to glutamate-receptors; (b) synergism of kainate and glutamate released from presynaptic terminals; and (c) release of a toxic amount of glutamate or aspartate due to stimulation by kainate-receptors contained in presynapses (edited by Tatsuya TANAKA, *Frontier of Epileptic Research*, p18, 1994, 1st Japan Winter Conference on Brain Research, Life-Science Publishing).

In connection with clinical epileptic symptoms, the kinate model corresponds to a model for intractable temporal lobe epilepsy (injection to the amygdala or hippocampus) and to a model for intractable cortex epilepsy (injection to the sensorymotor field (Tatsuya *TANAKA, BIO Clinica*, 11(9), 695–697).

The excellent antiepileptic action of nefiracetam is proven through injection thereof to rats of the kainate model, one of the intractable epilepsy models. A high dose of nefiracetam clinically suppressed both a kainate-induced amygdala seizure and a cortex focal seizure, and the suppression was observed in an electrocephalogram. The degree of suppression is stronger in relation to a cortex focal seizure. The identical kainate model, proves that administration of nefiracetam suppresses hypermetabolism in the brain and propagation of a seizure from a focus. The suppression effect is stronger in the cortex. Since nefiracetam dose-dependently suppressed propagation of seizure related-hypermetabolism, the seizure-suppression mechanism of nefiracetam is based on suppression of seizure propagation. Furthermore, the above action corresponds to a suppression action of brain glucose metabolism predominantly in the cortex, in that nefiracetam exhibits a sedative action to rats.

Kainic acid, a strong neuroexitatory amino acid, is well known to induce a convulsive seizure through systemic administration or local administration in the brain. Injection of kainic acid in a microamount to one side of the amygdaloid of an animal such as a cat or rat induces status epilepticus of limbic system epilepsy in an acute phase and a spontaneous limbic system seizure in a chronic phase, to thereby realize a model for epilepsy similar to human temporal lobe epilepsy. The status epilepticus of a kainate-induced amygdala seizure in an acute phase is very severe, and only a high concentration of zonisamide among known antiepileptic agents has a proven suppression effect. Nefiracetam exhibited a suppression effect on a kainate-induced amygdala seizure in a dose as high as 200 mg/kg. However, the suppression effect was temporary and lasted for some minutes or some hours, and a seizure appeared again. Meanwhile, nefiracetam exhibited a remarkable suppression effect on a kainate-induced cortex focal seizure for all tested rats through administration in an amount of 100 mg/kg, and seizure suppression was maintained from immediately after administration of nefiracetam such that seizure never appeared again. Thus, nefiracetam was revealed to exhibit a suppression effect on both a kainate-induced amygdala seizure and a kainate-induced cortex focal seizure, and the suppression effect was revealed to be stronger to a cortex focal seizure.

In addition, in both models, nefiracetam was intravenously injected to rats to provide sedation, and algodiapholia and chalasia of quarters were observed. This indicated that nefiracetam suppresses functions of the entire cortex. Furthermore, the investigation with regard to the change in local glucose metabolism during a seizure revealed that administration of nefiracetam in an amount of 100 mg/kg lowers glucose metabolism throughout the entire brain in both the case of an amygdala seizure and the case of a cortex focal seizure. Particularly, glucose metabolism was lowered to below a normal level in portions of the cortex and the basal ganglia on the non-focal side. When the dose of nefiracetam increased, evolution of a hypermetabolism domain with seizure propagation was suppressed dose-dependently. A hypermetabolism domain was limited at a focus in the amygdala through administration at. 200 mg/kg. Such effects on glucose metabolism during a seizure indicate that nefiracetam suppresses propagation of a seizure. In addition, strong suppression of cerebral glucose metabolism and the basal ganglia indicates that nefiracetam is more effective in relation to a cortex focal seizure than in relation to a limbic system seizure, as shown in the observation of an electrocephlogram. A sedative action of nefiracetam at high concentration is considered to be attributed to affinity thereof to the cortex.

The manner of administration of the antiepileptic agents for intractable epilepsies of the present invention is not particularly limited, and the agents may be administered to humans perorally or parenterally. The above-described compound represented by formula (I), an active ingredient of the pharmaceuticals of the present invention, may be administered directly. However, typically, a pharmaceutical composition which is prepared by use of the compound represented by formula (I) and one or more pharmaceutically acceptable additives is preferably administered perorally or parenterally.

The dose of the pharmaceutical of the present invention is not particularly limited, and is appropriately selected in accordance with the manner of administration, severity of a symptom of epilepsy or seizures, frequency of seizures, object of administration, e.g., preventive or therapeutic, and age or weight of the patient. For example, the daily dose of the compound represented by formula (I) for an adult is 200–2,000 mg, preferably about 300–900 mg, and the daily dose may be divided. The timing of administration of the pharmaceutical of the present invention may also be appropriately selected. If the pharmaceutical is administered before onset of epileptic symptoms or seizures, it serves as an antiepileptic agent.

Examples of the form of formulation suitable for peroral administration include tablets, capsules, powders, granules, liquids, and syrups. Examples of the form of formulation suitable for parenteral administration include subcutaneous, intravenous, and intramuscular injections; drips; inhalants; percutaneous or premucosa absorption formulations; suppositories; and cataplasmas. Examples of pharmaceutically acceptable additives include excipients, disintegrators, disintegration aids, binders, lubricants, coatings, colorants, diluents, bases, solubilizers or solubilization aids, isotonic agents, pH-adjusters, propellants, and stickers.

For example, pharmaceutically acceptable additives may be incorporated into formulations suitable for peroral administration and percutaneous or permucosa administration. Examples of the additives include excipients such as glucose, D-mannitol, starch, and cryslalline cellulose; disintegrators or disintegration aids such as calcium carboxymethylcellulose; binders such as hydroxypropylcellulose, hydroxypropylmethylcellulose, polyvinylpyrrolidone, and gelatin; lubricants such as magnesium stearate and talc; coatings such as hydroxypropylmethylcellulose, sucrose, polyethylene glycol, and titanium oxide; and bases such as vaseline, liquid paraffin, polyethylene glycol, gelatin, kaolin, glycerin, purified water, and hard fat.

Furthermore, the formulations may be produced through incorporation of propellants such as Fron, diethyl ether, and compressed gas; stickers such as sodium polyacrylate, polyvinyl alcohol, methylcellulose, polyisobutylene, and polybutene; and base cloths such as cotton cloth and plastic sheets. Additives for formulation may be incorporated into formulations suitable for injections and drips, e.g., solubilizers or solubilization aids which serve as a component of injections which are aqueous or must be made soluble before use. Examples thereof include distilled water for injection, sodium chloride for injection, and propylene glycol. There may also be added isotonic agents such as glucose, sodium chloride, D-mannitol, and glycerin and pH-regulators such as inorganic and organic acids and inorganic and organic bases.

Nefiracetam, a typical pharmaceutical of the present invention, has an acute toxicity of 2,005 mg/kg (male mouse, peroral) and therefore, is highly safe (Japanese Patent Application Laid-Open (kokai) No. 5-163144).

EXAMPLES

The present invention will next be described in more detail by way of examples, which should not be construed as limiting the invention thereto.

[Method for preparing a kindling model] Male Wistar rats (weight: 200–250 g, Tokyo Jikken Dobutsu) were used, and pentobarbital (50 mg/kg, Dinabot) and ketamine (50 mg/kg, Sankyo Co., Ltd.) were used as anesthetic agents.

Each anesthetized rat was set in a stereotaxic apparatus (Type SR-6, Narishige Ikakiki K.K.), and the scalp of the rat was peeled to thereby expose the cranial bone. A small hole was drilled in the cranial bone by use of an electric drill (Model C-201, Urawa Kohgyo K.K.). Subsequently, in accordance with the brain atlas of Paxinos, G., Watson, C. (The Rat Brain in Stereotaxic Coordinates, Academic Press, New York, 1986), an electrode for chronic stimulation and recording (made of stainless steel with Teflon coating, outer diameter: about 250 $\mu$m, Nippon Koku Denshi) was implanted in the amygdala (shown in the left side of the brain atlas), and was firmly fixed on the cranial bone by use of dental cement in order to prevent disconnection thereof. Subsequently, after a recovery period of 1–2 weeks, a kindling stimulation was initiated. A kindling stimulation was performed for one second per day at an intensity of 200 $\mu$A with a sine wave of 50 Hz. (Apparatus used for the electrical stimulation produced by Nihon Kohden Kogyo Co.; Cat. No. 8-6207A.) A rat which exhibits seizure stage 5 for three or more consecutive days is considered a fully kindled rat. Generalized Seizure Threshold (GST) where seizure stage 5 is shown constantly was obtained from each of the fully kindled rats.

Example 1

A dose-response of nefiracetam (15–180 mg/kg) with respect to a kindling seizure induced GTS stimulation intensity was evaluated in terms of the following parameters: seizure stage, and afterdischarge duration at the sitimulated amygdala and motor seizure duration. The results are shown in Tables 1 through 3.

In accordance with the method of Racine et al. (Modification of seizure activity by electrical stimulation: II motor seizure. Electroencephalography Clin. Neurophysiol. 1972. 32: 281–294), seizures were classified into the following five stages: stage 1 (chewing); stage 2 (head nodding); stage 3 (forelimb clonus); stage 4 (rearing); and stage 5 (rearing and falling).

Motor seizure duration (seconds) was represented by the total duration of stages 3 through 5. Stage 1 or Stage 2 is a seizure symptom of the limbic system, and Stage 3, 4, or 5 is regarded a motor seizure (Sato, M., Racine, R. J., McIntyre, D. C., Kindling: basic mechanisms and clinical validity, Electroencephalography Clin. Neurophysiol. 1990, 76: 459–472).

Afterdischarge duration (seconds) was recorded by use of an electrode for recording, and was represented by the seizure-discharge duration shown in a electroencephalogram, which is induced by a kindling stimulation. Nefiracetam was dissolved into a solvent (0.5% carboxymethyl cellulose) and the solution was administered orally 90 minutes before GST stimulation, wherein the amount of administered nefiracetam is classified into several stages within a range of 15–180 mg/kg.

TABLE 1

The effect of nefiracetam on seizure stages in fully amygdala kindled rats

| Amount (mg/kg) | Number of samples | Change of stage (%) | Standard error | p value |
|---|---|---|---|---|
| 15 | 5 | 80.0 | 20.0 | .3739 |
| 30 | 5 | 100.0 | 0.0 | .0000 |
| 60 | 6 | 80.0 | 16.3 | .2752 |
| 90 | 5 | 76.0 | 4.0 | .0039 ** |
| 120 | 6 | 13.3 | 9.9 | .0003 ** |
| 180 | 5 | 36.0 | 22.3 | .0453 * |

Change of stage (%): Percentage of a seizure stage after administration of nefiracetam, with a seizure stage before administration thereof taken as 100.
Amount: The amount of administered nefiracetam.
p value: T-tested value of the rate of change with respect to the value before administration of nefiracetam (paired t-test).
* refers to p < 0.05; ** refers to p < 0.01.

TABLE 2

The effect of nefiracetam on motor seizure duration
(MSD) in fully amygdala kindled rats

| Amount (mg/kg) | Number of samples | Change of MSD (%) | Standard error | p value |
|---|---|---|---|---|
| 15 | 5 | 76.4 | 20.2 | .3072 |
| 30 | 5 | 96.0 | 9.4 | .6955 |
| 60 | 6 | 81.7 | 17.1 | .3321 |
| 90 | 5 | 78.0 | 19.8 | .3286 |
| 120 | 6 | 0.6 | 0.6 | <.0001 ** |
| 180 | 5 | 21.3 | 14.3 | .0054 ** |

Change of MSD (%): Percentage of MSD after administration of nefiracetam, with MSD before administration thereof taken as 100.
Amount: The amount of administered nefiracetam.
p value: T-tested value of the rate of change with respect to the value before administration of nefiracetam (paired t-test).
** refers to $p < 0.01$.

TABLE 3

Effect of nefiracetam on afterdischarge duration
(ADD) in fully amygdala kindled rats

| Amount (mg/kg) | Number of samples | Change of ADD (%) | Standard error | p value |
|---|---|---|---|---|
| 15 | 5 | 81.7 | 19.4 | .3997 |
| 30 | 5 | 99.9 | 7.9 | .9923 |
| 60 | 6 | 83.9 | 17.2 | .3898 |
| 90 | 5 | 82.3 | 21.9 | .4652 |
| 120 | 6 | 25.0 | 12.7 | .0020 ** |
| 180 | 5 | 24.8 | 16.0 | .0094 ** |

Change of ADD (%): Percentage of ADD after administration of nefiracetam, with ADD before administration thereof taken as 100.
Amount: The amount of administered nefiracetam.
p value: T-tested value of the rate of change with respect to the value before administration of nefiracetam (paired t-test).
** refers to $p < 0.01$.

For nefiracetam-administered rats, a dose-dependent inhibition was recognized in all three parameters: seizure stage (Table 1), motor seizure duration (Table 2), and afterdischarge duration (Table 3). By the least-squares method, a regression curve was obtained from the effect of nefiracetam on a seizure stage, and the regression curve was used to obtain 114 mg/kg of ED50.

Example 2

[Method] The rats used in this Example were of the same type in terms of the source of purchase, body weight, and age (week). For each rat, in the same manner as in of Example 1, there were performed anesthetization, setting of an electrode on the amygdala, fixation of the electrode at the cranial bone, and a kindling stimulation (50 Hz, sine wave).

For non-administered rats and nefiracetam-administered rats (120 mg/kg), the effect of the administration was evaluated when GST stimulation intensity was increased by a factor of two (GST 2) or three (GST 3). The effect of 120 mg/kg of nefiracetam on kindling seizures induced by one-fold, two-fold, and three-fold GTS stimulation was evaluated in terms of the following parameters: seizure stage, motor seizure duration, and afterdischarge duration. The results are shown in Tables 4 through 6.

TABLE 4

Effect of nefiracetam on seizure stages in fully
amygdala kindled rats at different stimulation intensities

| GST intensity | Number of samples | Change of stage (%) | Standard error | p value |
|---|---|---|---|---|
| 1-fold | 6 | 16.7 | 16.7 | .0041 ** |
| 2-fold | 5 | 14.7 | 14.7 | .0066 ** |
| 3-fold | 5 | 52.0 | 13.6 | .0240 * |

Change of stage (%): Percentage of a seizure stage after administration of nefiracetam, with a seizure stage before administration thereof taken as 100.
p value: T-tested value of the rate of change with respect to the value before administration of nefiracetam (paired t-test).
* refers to $p < 0.05$; ** refers to $p < 0.01$.

TABLE 5

Effect of nefiracetam on motor seizure duration
(MSD) in fully amygdala kindled rats at different
stimulation intensities

| GST intensity | Number of samples | Change of MSD (%) | Standard error | p value |
|---|---|---|---|---|
| 1-fold | 6 | 11.1 | 11.1 | .0005 ** |
| 2-fold | 5 | 15.2 | 9.5 | .0009 ** |
| 3-fold | 5 | 43.8 | 14.0 | .0159 * |

Change of MSD (%): Percentage of MSD after administration of nefiracetam, with MSD before administration thereof taken as 100.
p value: T-tested value of the rate of change with respect to the value before administration of nefiracetam (paired t-test).
* refers to $p < 0.05$; ** refers to $p < 0.01$.

TABLE 6

Effect of nefiracetam on afterdischarge duration
(ADD) in fully amygdala kindled rats at different stimulation
intensities

| GST intensity | Number of samples | Change of ADD (%) | Standard error | p value |
|---|---|---|---|---|
| 1-fold | 6 | 24.9 | 19.4 | .0118 * |
| 2-fold | 5 | 91.8 | 21.0 | .7171 |
| 3-fold | 5 | 95.5 | 7.0 | .5555 |

Change of ADD (%): Percentage of ADD after administration of nefiracetam, with ADD before administration thereof taken as 100.
p value: T-tested value of the rate of change with respect to the value before administration of nefiracetam (paired t-test).
* refers to $p < 0.05$, which indicates that the results are significant.

In the case of one-fold GST stimulation intensity, a significant and strong inhibition was shown in all parameters: seizure stage, motor seizure duration, and afterdischarge duration. In the case of two-fold GST stimulation intensity, a significant inhibition was shown in seizure stage and motor seizure duration, but an effect on afterdischarge duration was reduced. In the case of three-fold GST stimulation intensity, a significant inhibition was shown in seizure stage and motor seizure duration, but the effect was reduced as compared with the effect in the case of one-fold or two-fold GST stimulation intensity. In the case of two-fold GST intensity and the case of three-fold GST stimulation intensity, some samples maintained very low seizure stages or showed no behavioral seizures, althoughafterdischarge duration was almost restored to the value before the administration of nefiracetam.

From the above-described results, the effect of nefiracetam on kindling seizure may be related to the following two mechanisms: the increase of afterdischarge threshold at the seizure-induced site, and the inhibition of seizure spreading to the entirety of the brain.

Thus, nefiracetam may increase the seizure threshold at the seizure focus site and inhibit the seizure spreading, to thereby inhibit the expression of a seizure. Therefore, the drug of the present invention is effective for an intractable secondary-generalized seizure generated from the temporal lobe.

Example 3

In this test, the following parameters were evaluated: seizure stage in the process of development of amygdala kindling and afterdischarge duration at the stimulated amygdala.

[Method] Male Wistar rats (5 to 6 weeks old, weight: 200–250 g, Tokyo Jikken Dobutsu) were used. For each rat, in a manner similar to that in Example 1, there were performed anesthetization, setting of an electrode on the amygdala, and fixation of the electrode at the cranial bone. After a recovery period of at least two weeks, kindling stimulation was initiated.

Kindling stimulation was performed for one second per day with a sine wave of 50 Hz. On the first day, the afterdischarge threshold was determined, and from the second day, kindling stimulation was performed at the intensity of the threshold. On the first day, nefiracetam was not administered, in order to determine the threshold. For twenty days from the second day, a dose of nefiracetam (45, 90, or 180 mg/kg) was administered orally, and then kindling stimulation was performed 90 minutes after administration. After nefiracetam was administered for twenty days, kindling stimulation was performed without administration for an additional seven days.

TABLE 7

Effect of nefiracetam on establishment of a kindling seizure (change in afterdischarge threshold)

|  | Number of samples showing stage 5 intermittently/ total samples | Number of samples showing an increase in afterdischarge threshold/total samples |
|---|---|---|
| Test 1 |  |  |
| Control samples | 0/5 | 0/5 |
| Nefiracetam 90 mg/kg | 4/6 | 3/6 |
| Test 2 |  |  |
| Control samples | 0/5 | 0/5 |
| Nefiracetam 45 mg/kg | 0/4 | 0/4 |
| Nefiracetam 180 mg/kg | 5/6 | 2/6 |

TABLE 8

Effect of administration of nefiracetam (90 mg/kg) on the development of an seizure stage (a typical example)

| Day | 1 | 2 | 3 | 4 | 5 | 6 | 7 | 8 | 9 | 10 |
|---|---|---|---|---|---|---|---|---|---|---|
| Stimulation intensity (μA) | 50 | 50 | 50 | 50 | 50 | 50 | 50 | 50 | 50 | 50 |
| Control samples | 0 | 0 | 1 | 1 | 3 | 4 | 4 | 4 | 5 | 5 |
| Stimulation intensity (μA) | 50 | 50 | 50 | 50 | 50 | 50 | 50 | 50 | 50 | 50 |
| Nefiracetam administration | 0 | 0 | 0 | 0 | 0 | 1 | 3 | 4 | 4 | 5 |
| Day | 11 | 12 | 13 | 14 | 15 | 16 | 17 | 18 | 19 | 20 |
| Stimulation intensity (μA) | 50 | 50 | 50 | 50 | 50 | 50 | 50 | 50 | 50 | 50 |
| control samples | 5 | 5 | 5 | 5 | 5 | 5 | 5 | 5 | 5 | 5 |
| Stimulation intensity (μA) | 150 | 50 | 100 | 75 | 75 | 75 | 50 | 50 | 100 | 125 |
| Nefiracetam administration | 4 | 4 | 0 | 4 | 4 | 4 | 4 | 4 | 5 | 0 |
| Day | 21 | 22 | 23 | 24 | 25 | 26 | 27 | 28 |  |  |
| Stimulation intensity (μA) | 50 | 50 | 50 | 50 | 50 | 50 | 50 | 50 |  |  |
| Control samples | 5 | 5 | 5 | 5 | 5 | 5 | 5 | 5 |  |  |
| Stimulation intensity (μA) | 100 | 50 | 50 | 50 | 50 | 50 | 50 | 50 |  |  |
| Nefiracetam administration | 5 | _5_ | _5_ | _5_ | _5_ | _5_ | _5_ | _5_ |  |  |

On and after the 22nd day, an underlined number refers to the case where nefiracetam was not administered.

Table 8 shows the process of seizure development in a typical example of a non-administered rat and a nefiracetam-administered rat (90 mg/kg) in this test. As is apparent from Table 8, in the case of a non-administered control rat, a stage began to progress on the third day and reached stage 5 on the ninth day.

Subsequently, a non-administered rat maintained stage 5 until the 28th day, the last day of the test. Non-administered rats showed no examples of increased afterdischarge threshold (see Table 7).

In contrast, in the case of a nefiracetam-administered rat (90 mg/kg), a stage began to progress on the sixth day and continued to progress as in the case of the non-administered rat and reached stage 5 on the tenth day (see Table 8).

In one case of a nefiracetam-administered rat, afterdischarge was not induced in spite of afterdischarge threshold stimulation. In this case, electrical stimulation was increased in steps of 25 µA until afterdischarge was shown. On the eleventh day, afterdischarge was shown at 150 µA and seizure stage was 4. Subsequently, afterdischarge threshold had changed, and the rise and fall of the threshold was repeated several times (see Table 8). Such a rise of afterdischarge threshold was shown in the cases of nefiracetam administration of 90 and 180 mg/kg (see Table 7). As is apparent from Table 7, even in the case of no rise of afterdischarge threshold, in one case stage 5 was intermittently expressed. As is described above, after the completion of stage 5, a difference was apparent between non-administered rats and nefiracetam-administered rats, in the change of stage and in the threshold (see Table 7).

In this test, no difference was observed between nefiracetam-administered rats and non-administered control rats in the number of stimulations until the completion of stage 5. However, after completion of stage 5, nefiracetam-administered rats exhibited "returning" of a seizure stage more frequently than did control rats. In the normal process of seizure development, once a seizure reached stage 5, this stage was expressed constantly.

Afterdischarge threshold is known to decrease in accordance with the development of seizure in the normal process of seizure development. However, as a result of administration of nefiracetam, afterdischarge threshold apparently rose during the expression of stages 3 through 5; i.e., expression of a motor seizure. Such a phenomenon has not been exhibited in the case of administration of known drugs. Additionally, administration of nefiracetam prevented the expression of stage 5, even when afterdischarge threshold did not rise.

As described above, nefiracetam comprises a new mechanism which affects the process of kindling development.

Example 4-1

The antiepiletic action of nefiracetam was studied by use of two partial seizure models; i.e., models for amygdala seizures and cortical focal seizures, both of which are caused by local injection. of kainic acid. Specifically, effects on clinical seizure, on electroencephalogram observations, and on glucose metabolism in the brain during a seizure were studied.

I. Study of Kainate-induced Amygdala Seizures:

Seizure suppressing effects of nefiracetam on amygdala seizures and changes in electroencephalogram observations were studied.

[Method for measuring an electrophysiological effect] The following operation was performed by use of 19 Wistar male rats (Japan SLC Co.) each having a weight of 250–350 g. Each rat was anesthetized by pentobarbital and fixed in a stereotaxic apparatus. A stainless steel cannula having an outer diameter of 0.6 mm was inserted into the left bilateral amygdala of the rat so as to inject kainic acid (Pellegrino, A. S., Cushman, A. J., A Stereotaxic Atlas of the Rat Brain, Plenum Press, New York, 1979, inserted position: A, +5.0; L, +5/0; D, -3.0). Subsequently, a bipolar depth electrode having a diameter of 0.2 mm were inserted into bilateral amygdala (A, +5.0; L, +-5.0; D, -3.0) and hippocampus (A, +3.0; L, +-3.2; D, +1.5). Screw electrodes were set at the left sensorimotor area (A, +1.0 (from bregam); L, +-2.5; D, 0.5 (from dura)), frontal sinus, and occipital median. The electrodes were connected to sockets, and the cannula, the electrodes, and the sockets were fixed on the cranium by use of dental cement. Seven days after operation, 1 µL of a solution of kainic acid dissolved in phosphoric acid buffer (1 mg/ml) was injected through the cannula (rate: 0.8–1.0 mL/min) (n=12), so as to induce limbic system seizures. The electrodes were connected to an electroencephalograph, and the behavior of the rat in a cage was observed. An electroencephalogram was recorded by use of the electrode at the frontal sinus serving as an indifferent electrode and the electrode at the occipital median serving as ground. The behavior and electroencephalogram were simultaneously recorded by use of a video electroencephalogram recorder based on an electroencephalograph (SYNAFIT 1000; NEC San-ei Instruments, LTD.).

One to two hours after the injection of kainic acid, when a limbic system seizure was in status epilepticus, nefiracetam dissolved in saline (10 mg/mL) was slowly injected into a caudal vein in an amount selected from 10, 50, 100, and 200 mg/kg (n=12). The same amount of saline was injected into a vein of rats of the control group (n=7). Subsequently, behavior and electroencephalograms of the rat were continuously recorded for at least eight hours, followed by two-hour recording after 24 hours, 48 hours, and 72 hours. Changes in clinical seizure and electroencephalogram observations just after the injection of the nefiracetam solution or saline, and occurrence of seizures and electroencephalogram observations after 24, 48, and 72 hours were measured, and the results were evaluated on the basis of the comparison.

[Results] After injection of kainic acid in the amygdala during rest and during wakefulness at rest, low-amplitude polyspikes appeared within 20 minutes, and the polyspikes continued to appear. Within a short time, rhythmic high-amplitude spikes appeared with clinical seizures, and seizure waves reached the hippocampus on the same side and the amygdala and the hippocampus on the other side. The clinical seizures were typical limbic system seizures, exhibited symptoms such as rotating the head toward the right, attention response, akinesis, sialorrhea, and prosopospasm. Subsequently, the seizures reappeared at 5- to 10-minute intervals and progressed in status epilepticus. Rats intravenously injected with nefiracetam in an amount of 10, 50, or 100 mg/kg during the status epilepticus showed no apparent changes in paroxysmal behavior or electroencephalograms (Tables 9 and 10). However, rats injected in an amount of 100 mg/kg were sedated, their eyes closed, and their limbs were relaxed. At that time, the rats showed no reaction to pain stimulation, and the sedative action continued for 30–60 minutes after injection. In 5 out of 8 rats injected in an amount of 200 mg/kg, seizures disappeared from just after the injection to 5 minutes or 4 or more hours, and then seizures reappeared (Table 9).

In 4 out of the 5 rats, spikes corresponding to the amygdala disappeared from an electroencephalogram. In the remaining rat, spikes corresponding to the amygdala on the other side and corresponding to the hippocampus on both sides disappeared, and spikes corresponding to the amygdala on the injected side remained. Although seizures of one rat disappeared just after the injection of nefiracetam, the rat died 25 minutes later. In 2 rats, spikes corresponding to the amygdala disappeared after 24, 48, and 72 hours (Table 10). In 3 out of the 8 rats, seizures were not suppressed in terms of behavior and an electroencephalogram, even though the rats were injected with 200 mg/kg of nefiracetam. In the 3 rats, spikes corresponding to the amygdala remained after 24 , 48, and 72 hours. The 8 rats injected in an amount of 200 mg/kg and rats injected in an amount of 100 mg/kg were sedated for approximately 60–90 minutes from just after the injection, and awoke after seizure waves reappeared on the electroencephalogram. Such a sedative action was not observed in the case of injection of nefiracetam in an amount of 10 or 50 mg/kg.

TABLE 9

Suppressing effect of nefiracetam on kainate-induced amygdala seizures

| Rat | Nefiracetam dosage | Disappearance of seizures intravenous injection | Disappearance period of seizures after intravenous injection | Sedative action |
|---|---|---|---|---|
| C1 | NS | − | ND | − |
| C2 | NS | − | ND | − |
| C3 | NS | − | ND | − |
| C4 | NS | − | ND | − |
| C5 | NS | − | ND | − |
| C6 | NS | − | ND | − |
| C7 | NS | − | ND | − |
| N1 | 200 mg/kg | + | 2 h 33 min | + |
| N2 | 200 | − | ND | + |
| N3 | 200 | − | ND | + |
| N4 | 200 | − | ND | + |
| N5 | 200 | + | (died after 25 min) | + |
| N6 | 200 | + | 5 min. | + |
| N7 | 200 | + | 4 h 32 min | + |
| N8 | 200 | + | 35 min | + |
| N9 | 100 | − | ND | + |
| N10 | 100 | − | ND | + |
| N11 | 50 | − | ND | − |
| N12 | 10 | − | ND | − |

C1–C7: control group, N1–N10: nefiracetam adininistered group, NS: saline, ND: no data, (+): effective, (−): ineffective, h: hours, min: minutes

TABLE 10

Effects of nefiracetam on change in electroencephalogram observations of the amygdala corresponding to kainate-induced amygdala seizures

| Rat | Nefiracetam dosage | Spikes from the amygdala just after intravenous injection | Spikes from the amygdala after 24 h | Spikes from the amygdala after 48 h | Spikes from the amygdala after 72 h |
|---|---|---|---|---|---|
| C1 | NS | + | + | + | + |
| C2 | NS | + | + | + | − |
| C3 | NS | + | + | + | − |
| C4 | NS | + | + | + | + |
| C5 | NS | + | + | + | + |
| C6 | NS | + | + | − | − |
| C7 | NS | + | + | − | − |
| N1 | 200 mg/kg | − | − | − | − |
| N2 | 200 | + | − | − | − |
| N3 | 200 | + | + | + | + |
| N4 | 200 | + | + | + | + |
| N5 | 200 | − | − | ND | ND |
| N6 | 200 | − | + | + | + |
| N7 | 200 | − | − | − | − |
| N8 | 200 | + (spikes disappeared out of focal point) | + | ND | ND |
| N9 | 100 | + | + | ND | ND |
| N10 | 100 | + (decline of amplitude) | + | ND | ND |
| N11 | 50 | + | + | ND | ND |
| N12 | 10 | + | + | ND | ND |

C1–C7: control group, N1–N10: nefiracetam administered group, NS: saline, ND: no data, (+): effective, (−): ineffective, h: hours Example 4-2

I-2. Study of Change in Local Cerebral Glucose Metabolism

Effects of nefiracetam on local cerebral glucose metabolism during an amygdala seizure were studied.

[Method for measuring cerebral glucose metabolism] Cannulas for injection of kainic acid were inserted in an assigned position of the left side of the amygdala of 18 Wistar male rats and fixed through the same procedure as described in Example I-1. Seven days after operation, polyethylene catheters were set and fixed to the femoral artery and vein of one side under halothane anesthesion, and the lower half of the body of each rat were put in plaster so as to prevent removal of the catheter. Upon awakening from narcotism, the same kainic acid solution as described in I-1 (1 $\mu$L) was injected through the cannula so as to induce seizures. After elapse of 90 minutes from injection of kainic acid, when limbic system seizures were in status epilepticus, 50, 100, or 200 mg/kg of nefiracetam was intravenously injected, whereas saline was injected into rats of the control group. After 60 minutes, 25 $\mu$Ci of [$^{14}$C] deoxyglucose was intravenously injected. After the tracer was injected, blood was continuously collected from the artery for 45 minutes. When collection was finished, heads were cut off. Brains were extirpated immediately and instantly frozen in by hexane (−25° C.) cooled by dry ice. The frozen brain was sliced in a cryostat (−20° C.) so as to produce coronary, serial-frozen sections having a thickness of 20 $\mu$m. Subsequently, the sections were dried and put on high-speed X-ray film with a [$^{14}$C] standard, followed by seven-day-exposure in a cassette to thereby obtain an autoradiogram. The blood samples collected from the artery were centrifuged so as to collect plasma, the [$^{14}$C] radioactivity was measured by use of a liquid scintillation counter, and glucose concentration in plasma was measured.

The optical density of the intracerebral structure of each section was measured from the autoradiogram by use of a densitometer, and a glucose utilization rate of each intracerebral structure was calculated by use of the formula of Sokoloff (Sokoloff, L., Reivich, M., Kennedy, C., et al., *J. Neurochemistry*, 28: 897–916, 1977) based on [$^{14}$C] radioactivity and glucose concentration in plasma. The obtained data were compared quantitatively and statistically with those of the control group, through the Mann-Whitney U-test.

[Results] Table 11 shows the local glucose metabolism rate of each intracerebral structure of the control group (nefiracetam non-dosage group) and the 100 mg/kg nefiracetam-administered group during amygdala seizures. In the control group, glucose metabolism in the occipitoparietal cortex, temporal lobe cortex, sensorimotor area, and caudatum-putamen on the focal side; the limbic system such as the amygdala and the hippocampus on both sides; and the thalamus and substantia nigra in the focal side are promoted as compared with glucose metabolism of normal rats. When 100 mg/kg of nefiracetam is administered, glucose metabolism shows no change in the sensorimotor area, caudatum-putamen, amygdala, and hippocampus on the focal side. In contrast, in almost all other regions, where glucose metabolism shows a high rate in the non-dosage group, promotion of glucose metabolism is suppressed (Table 12). Furthermore, glucose metabolism is suppressed in all regions in the cerebral cortex, thalamus, hypothalamus, and brain stem reticular formation on the non-focal side, where almost no changes are observed even in the control group, i.e., local glucose metabolism in these regions is lower than in normal rats. Such a suppression of cerebral glucose metabolism caused by nefiracetam can be described as follows; when 50 mg/kg of nefiracetam is administered, the amygdala, hippocampus, and cerebral cortex on the non-focal side is suppressed slightly; when 100 mg/kg of nefiracetam is administered, suppression of glucose metabolism is also observed in the hippocampus and the cerebral cortex on the focal side; and when 200 mg/kg of nefiracetam is administered, the amygdala on the focal side is the only region where the metabolism is prompted. In other words, nefiracetam suppresses extension of the area where glucose metabolism is high, in a dose-responsive manner. In addition, when 100 or 200 mg/kg of nefiracetam was administered to a rat, the same sedative action as described in I-1 was observed.

TABLE 11

Local glucose metabolism rate in each intracerebral structure during kainate-induced amygdala seizures (comparison of nefiracetam non-dosage group and administered group)

| Intracerebral structure | Nefiracetam non-dosage | | Nefiracetam-administered (100 mg/kg) | |
|---|---|---|---|---|
| | Focal side | Non-focal side | Focal side | Non-focal side |
| Frontal lobe cortex | 109.3 ± 3.6 | 82.0 ± 1.9 | 81.8 ± 5.7* | 65.7 ± 3.6** |
| Parietal lobe cortex | 129.7 ± 8.3 | 83.6 ± 2.7 | 108.8 ± 10.6 | 72.1 ± 4.9 |
| Occipital lobe cortex | 165.2 ± 20.2 | 102.0 ± 9.8 | 139.2 ± 5.6 | 78.6 ± 5.8 |
| Temporal lobe cortex | 121.7 ± 11.0 | 84.7 ± 5.4 | 102.6 ± 6.2 | 67.8 ± 3.5* |
| Sensorimotor area cortex | 137.9 ± 6.6 | 91.7 ± 4.9 | 139.1 ± 9.0 | 73.4 ± 4.7* |
| Corpus callosum | 21.0 ± 2.0 | 21.5 ± 1.9 | 21.9 ± 1.1 | 21.1 ± 1.1 |
| Candatum-putamen | 195.8 ± 17.2 | 9.3 ± 5.6 | 206.7 ± 16.5 | 73.1 ± 2.5** |
| Amygdala | 212.3 ± 4.3 | 92.3 ± 3.5 | 200.8 ± 4.5 | 66.2 ± 3.8** |
| hippocampus | 202.8 ± 10.7 | 145.0 ± 19.4 | 184.1 ± 7.1 | 87.2 ± 8.9* |
| Septal area | 143.4 ± 11.4 | 87.0 ± 4.5 | 117.1 ± 22.7 | 56.9 ± 3.3** |
| Thalamus | 121.9 ± 12.6 | 92.2 ± 2.9 | 90.5 ± 3.8* | 72.3 ± 2.8* |
| Hypothalamaus | 91.5 ± 6.3 | 71.9 ± 3.1 | 70.6 ± 4.7* | 58.5 ± 4.5* |
| Substantia nigra | 121.8 ± 6.7 | 61.8 ± 4.3 | 77.6 ± 6.8* | 45.9 ± 2.7* |
| Brain stem reticular formation | 61.5 ± 1.9 | 60.1 ± 1.8 | 52.9 ± 3.5 | 49.6 ± 3.3** |
| Cerebellar cortex | 51.0 ± 1.9 | 52.3 ± 1.6 | 47.2 ± 2.5 | 46.1 ± 2.1* | nefiracetam administered (100 mg/kg; 1 group 7 heads)
nefiracetam non-administered (1 group 7 heads)
data: average ± standard error ($\mu$mol/min/g)
*: $P < 0.05$,
**: $P < 0.01$ (Mann-Whitney U-test)

TABLE 12

Effects of nefiracetam on local cerebral glucose metabolism rate during kainate-induced amygdala seizures

| | Nefiracetam dosage (mg/kg) | | | | | |
|---|---|---|---|---|---|---|
| | 50 | | 100 | | 200 | |
| Intracerebral structure | Focal side | Non-focal side | Focal side | Non-focal side | Focal side | Non-focal side |
| Frontal lobe cortex | → | → | ↓ | ↓ | ↓ | ↓ |
| Parietal lobe cortex | → | → | →↓ | →↓ | ↓ | ↓ |
| Occipital lobe cortex | → | → | →↓ | →↓ | ↓ | ↓ |
| Temporal lobe cortex | → | → | →↓ | ↓ | ↓ | ↓ |
| Sensorimotor area cortex | → | → | → | ↓ | ↓ | ↓ |

TABLE 12-continued

Effects of nefiracetam on local cerebral glucose metabolism rate during kainate-induced amygdala seizures

| | Nefiracetam dosage (mg/kg) | | | | | |
|---|---|---|---|---|---|---|
| | 50 | | 100 | | 200 | |
| Intracerebral structure | Focal side | Non-focal side | Focal side | Non-focal side | Focal side | Non-focal side |
| Corpus callosum | → | → | → | → | → | → |
| Candatum-putamen | → | →↓ | → | ↓↓ | ↓ | ↓↓ |
| Amygdala | → | → | → | ↓↓ | ↓ | ↓↓ |
| hippocampus | →↓ | ↓ | ↓ | ↓↓ | ↓↓ | ↓↓ |
| Septal area | → | → | ↓ | ↓↓ | ↓↓ | ↓↓ |
| Thalamus | → | ↓ | ↓ | ↓↓ | ↓↓ | ↓↓ |
| Hypothalamaus | → | → | ↓ | →↓ | ↓ | ↓ |
| Substantia nigra | → | → | ↓ | ↓ | ↓ | ↓ |
| Brain stem reticular formation | → | → | →↓ | ↓ | ↓ | ↓ |
| Cerebellar cortex | → | → | → | ↓ | → | → |

→ : no change
→↓ : decreased in a low degree
↓ : decreased in a moderate degree
↓↓ : decreased in a high degree Example 5-1

II. Study of Kainate-induced Cortical Focal Seizures:

Seizure suppression effects of nefiracetam on cortical focal seizures and changes in electroencephalogram observations were studied.

[Method for measuring an electrophysiological effect] A stereotaxic operation was performed through the same manner as described in I-1 by use of Wistar male rats. A cannula was inserted in the left sensorimotor area for injection of kainic acid, and the cannula was simultaneously used as an electrode. A bipolar depth electrode was set in the bilateral caudatum, and screw electrodes were set in the right sensorimotor area, frontal sinus, and occipital bone. Seven days after operation, 1 $\mu$L of kainic acid solution (2 mg/mL) was injected so as to induce cortical focal seizures. After elapse of 1–2 hours from the injection of kainic acid, the same nefiracetam solution as described in I-1 (100 mg/kg) was intravenously injected, and behavior and electroencephalograms were recorded by use of a video electroencephalogram recorder. Suppression of seizures just after the administration of nefiracetam, changes in electroencephalograms, occurrence of seizures thereafter, and electroencephalogram observations were compared with those of the control group.

[Results] After injection of kainic acid into the cortex of the left sensorimotor area during rest and during wakefulness at rest, low-amplitude polyspikes appeared within 20 minutes in the left sensorimotor area and the caudatum-putamen, and the polyspikes continued to appear. Within a short time, rhythmic high-amplitude spikes appeared, and simultaneously, clonic seizures started to occur on the right upper extremity and the face. Seizure waves instantaneously reached the sensorimotor area and the caudatum-putamen on the other side. Subsequently, the seizures reappeared at 5- to 10-minute intervals, and tonic seizures on the right upper extremity and secondary generalized seizures were also observed. When such partial seizures were in status epilepticus, nefiracetam (100 mg/kg) was intravenously injected into the rat. As a result, the seizures disappeared immediately and the frequency of spikes on electroencephalograms decreased remarkably. In one rat, spikes corresponding to the right sensorimotor area on the other side and corresponding to the right caudatum-putamen almost disappeared (Table 13).

In addition, just after the intravenous injection of nefiracetam, the rats were sedated, closed their eyes, and their limbs were relaxed, and then awoke within 60 minutes, in the same manner as in the experiment of I. However, seizures did not appear after awakening. Also, only interictal discharges appeared in the electroencephalogram, and the frequency of the discharges decreased gradually. After 24 hours, similar to the case of the control group, myoclonic seizures corresponding to spikes on an electroencephalogram were observed in one rat. In contrast, seizures disappeared completely in two other rats.

TABLE 13

Suppressing effect of nefiracetam on kainate-induced cortical focal seizures

| Rats | Disappear of seizures | Reappear of seizures | Decrease of Spikes | Spikes after 24 hours | Sedative action |
|---|---|---|---|---|---|
| CC1 | − |  | − | + | − |
| CC2 | − |  | − | + | − |
| CC3 | − |  | − | + | − |
| DC1 | + | − | + | − | + |
| DC2 | + | − | + | + | + |
| DC3 | + | − | + | + | + |

CC1–CC3: control group
DC1–DC3: nefiracetam administered group
(+): effective, (−): ineffective Example 5-2

II-2. Study of Change in Cerebral Glucose Metabolism

Effects of nefiracetam on local cerebral glucose metabolism during a cortical focal seizure were studied.

[Method] A cannula was set in the left sensorimotor area of rats, and kinic acid was injected so as to induce seizures through the same manner as described in the experiment of I-1. Subsequently, a nefiracetam solution (100 mg/kg) was intravenously injected into each rat. After 60 minutes, [$^{14}$C] deoxyglucose was intravenously injected, and autoradiograms were produced through the same procedure as described in the experiment of I-2. A glucose utilization rate of each intracerabral structure was compared with that of the control group.

[Results] During kainate-induced cortical focal seizures, local glucose metabolism is promoted in the sensorimotor area which is the focal region; and the frontal lobe and parietal lobe cortex on the same side both of which connect to the sensorimotor area. Cerebral glucose metabolism is also promoted in caudatum-putamen, thalamus, and hippocampus on both sides. Furthermore, glucose metabolism is promoted in the sensorimotor area on the non-focal side of a rat. In the case nefiracetam (100 mg/kg) is intravenously injected during seizures, hypermetabolism is suppressed remarkably in the sensorimotor area, caudatum-putamen, and thalamus in the non-focal side and the hippocampus in both sides. In addition, nefiracetam suppresses extension of the area, where glucose metabolism is increased, in the cortex of the focal side (Table 14). Similar to the case of amygdala seizures, glucose metabolism is suppressed in the whole brain. Especially, the metabolism is suppressed strongly in a distant region.

TABLE 14

Effects of nefiracetam on change in local cerebral glucose metabolism rate during a cortical focal seizure

| | Nefiracetam (100 mg/kg) | |
|---|---|---|
| Intracerebral structure | Focal side | Non-focal side |
| Frontal lobe cortex | →↓ | ↓ |
| Parietal lobe cortex | ↓ | ↓↓ |
| Occipital lobe cortex | →↓ | ↓ |
| Teniporal lobe cortex | →↓ | ↓ |
| Sensorimotor area cortex | →↓ | ↓ |
| *Corpus callosum* | → | → |
| Candatum-putamen | ↓ | ↓↓ |
| Amygdala | →↓ | →↓ |
| Hippocampus | ↓↓ | ↓↓ |
| Septal area | →↓ | →↓ |
| Thalamus | →↓ | ↓ |
| Hypothalamaus | ↓ | ↓ |
| *Substantia nigra* | →↓ | →↓ |
| Brain stem reticular formation | →↓ | →↓ |
| Cerebellar cortex | → | → |

→: no change
→↓: decreased in a low degree
↓: decreased in a moderate degree
↓↓: decreased in a high degree Industrial Applicability The pharmaceuticals of the present invention are effective for human intractable epilepsy, specifically for temporal lobe epilepsy, cortex epilepsy, localization-related epilepsy, relapsed epilepsy following surgery for epilepsy, epilepsy following brain surgery, or traumatic epilepsy. In addition, the pharmaceuticals are effective for seizures associated with epilepsy such as secondary generalized seizures, complex partial seizures, and status epilepticus.

What is claimed is:

1. A method for treating an epilepsy, an intractable epilepsy or epileptic seizure, comprising:
   administering to a subject in need thereof an effective amount of a composition comprising as an active ingredient a compound of formula (I):

$$R^2-CH_2CONH-R^1 \quad (I)$$

wherein
   $R^1$ is a phenyl group or a pyridyl group, either of which may have one or more substituents, which may be identical or different, selected from the group consisting of $C_1$–$C_3$ alkyl group and hydroxyl group, and
   $R^2$ is a 2-oxo-1-pyrrolidinyl group which may have one or more substituents, which may be identical or different, selected from the group consisting of a halogen atom, a hydroxyl group, and a $C_1$–$C_3$ alkyl group;
   a salt of said compound,
   or hydrate of said compound or said salt of said compound.

2. The method of claim 1, wherein the intractable epilepsy is selected from the group consisting of localization-related epilepsy, generalized epilepsy and syndromes thereof.

3. The method of claim 2, wherein the intractable epilepsy is idiopathic or symptomatic.

4. The method of claim 2, wherein the localization-related epilepsy is cortical epilepsy or temporal lobe epilepsy.

5. The method of claim 4, wherein the cortical epilepsy is a frontal lobe epilepsy, parietal lobe epilepsy, or occipital lobe epilepsy.

6. The method of claim 1, wherein the epilepsy is West syndrome, Lennox syndrome, or a child symptomatic syndrome.

7. The method of claim 1, wherein the seizure is a secondary generalized seizure or a complex partial seizure.

8. The method of claim 1, wherein the intractable epilepsy or epileptic seizure is status epilepticus.

9. The method of claim 1, wherein the intractable epilepsy or epileptic seizure is an epilepsy following brain surgery, a traumatic epilepsy, or a relapsed epilepsy, following surgery for intractable epilepsy.

10. The method of claim 1, wherein the intractable epilepsy or epileptic seizure is an intractable localization-related epilepsy, an intractable secondary generalized seizure, an intractable complex partial seizure or an intractable status epilepticus.

11. The method of claim 1, wherein the compound represented by formula (I) is N-(2,6-dimethylphenyl)-2-(2-oxo-1-pyrrolidinyl)acetamide.

* * * * *

UNITED STATES PATENT AND TRADEMARK OFFICE
CERTIFICATE OF CORRECTION

PATENT NO. : 6,365,621 B1
DATED : April 2, 2002
INVENTOR(S) : Tanaka et al.

It is certified that error appears in the above-identified patent and that said Letters Patent is hereby corrected as shown below:

<u>Title page,</u>
Item [73], the Assignee information is incorrect. It should read as follows:
-- [73] Assignee: Daiichi Pharmaceutical Co., Ltd., Tokyo (JP) --

Signed and Sealed this

Twenty-fourth Day of September, 2002

*Attest:*

JAMES E. ROGAN
*Attesting Officer*     *Director of the United States Patent and Trademark Office*